United States Patent
Petry et al.

(10) Patent No.: US 6,596,742 B1
(45) Date of Patent: Jul. 22, 2003

(54) SUBSTITUTED 3-PHENYL-5-ALKOXY-1,3,4-OXADIAZOL-2-ONES, THEIR PREPARATION AND THEIR USE IN MEDICAMENTS

(75) Inventors: Stefan Petry, Frankfurt (DE); Karl Schoenafinger, Alzenau (DE); Guenter Mueller, Sulzbach (DE); Karl-Heinz Baringhaus, Wölfersheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/655,373

(22) Filed: Sep. 5, 2000

(30) Foreign Application Priority Data

Sep. 4, 1999 (DE) .......................... 199 42 354

(51) Int. Cl.[7] .................. A61K 31/4245; C07D 271/10
(52) U.S. Cl. ........................ 514/364; 548/144
(58) Field of Search ................... 548/144; 514/364

(56) References Cited

U.S. PATENT DOCUMENTS

| 4,076,824 A | 2/1978 | Boesch ............... 424/272 |
| 4,150,142 A | 4/1979 | Boesch ............... 424/272 |
| 5,093,343 A | 3/1992 | Bonse et al. ........... 514/363 |
| 5,236,939 A | 8/1993 | Bonse et al. ........... 514/364 |

FOREIGN PATENT DOCUMENTS

| DE | 2603877 | 8/1976 |
| DE | 2604110 | 8/1976 |
| EP | 0 048 040 | 3/1982 |
| EP | 0 067 471 | 12/1982 |
| EP | 143440 | * 6/1985 |
| EP | 0 419 918 | 4/1991 |
| GB | 0 518 042 | 7/1978 |
| WO | WO 96/13264 | 5/1996 |

* cited by examiner

Primary Examiner—Joseph K. McKane
Assistant Examiner—Golam M. M. Shameem
(74) Attorney, Agent, or Firm—Finnegan, Henderson, Farabow, Garrett & Dunner, LLP

(57) ABSTRACT

Substituted 3-phenyl-5-alkoxy-1,3,4-oxadiazol-2-ones of the formula 1

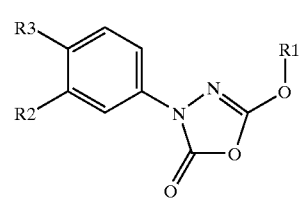

in any optically isomeric form, and their physiologically acceptable salts, where $R^1$ is $C_1$–$C_6$-alkyl, $C_3$–$C_9$-cycloalkyl, both of which may be unsubstituted or substituted, and $R^2$ and $R^3$ independently of one another are hydrogen, $C_6$–$C_{10}$-aryl, $C_3$–$C_8$-cycloalkyl, $C_6$–$C_{10}$-aryloxymethyl, O-benzyl, O—$C_6$–$C_{10}$-aryl, O—$C_3$–$C_8$-cycloalkyl, O—$C_1$–$C_6$-alkyl, $SO_2$—NH—$C_1$–$C_6$-alkyl, $SO_2$—NH-(2,2,6,6-tetramethylpiperidin-4-yl), $SO_2$—NH—$C_3$–$C_8$-cycloalkyl, $SO_2$—N($C_1$–$C_6$-alkyl)$_2$ or COX, where X is O—$C_1$–$C_6$-alkyl, NH—$C_1$–$C_6$-alkyl, NH—$C_3$–$C_8$-cycloalkyl or N($C_1$–$C_6$-alkyl)$_2$, with the proviso that the substitutents $R^2$ and $R^3$ may in some instances be unsubstituted or substituted and are not both simultaneously hydrogen. A process for their preparation, and their inhibitory effect on the hormone-sensitive lipase, HSL.

13 Claims, No Drawings

SUBSTITUTED 3-PHENYL-5-ALKOXY-1,3,4-OXADIAZOL-2-ONES, THEIR PREPARATION AND THEIR USE IN MEDICAMENTS

This application claims the benefit of foreign priority under 35 U.S.C. §119 to German patent application no. 19942354.7, filed on Sep. 4, 1999. The contents of that priority document are specifically incorporated by reference herein.

The invention relates to substituted 3-phenyl-5-alkoxy-1,3,4-oxadiazol-2-ones which have an inhibitory effect on the hormone-sensitive lipase HSL.

Certain 5-alkoxy-1,3,4-oxadiazol-2-ones having an ortho-substituted phenyl ring as substituent or having fused-on five- or six-membered rings have anthelmintic (DE-A 26 04 110) and insecticidal action (DE-A 26 03 877, EP-B 0 048 040, EP-B 0 067 471).

Certain 5-phenoxy-1,3,4-oxadiazol-2-ones having an ortho-substituted phenyl ring as substituent have endoparasiticidal action (EP-A 0 419 918).

It is an object of the present invention to provide compounds having an inhibitory effect on the hormone-sensitive lipase HSL.

This object was achieved with the substituted 3-phenyl-5-alkoxy-1,3,4-oxadiazol-2-ones of the formula 1,

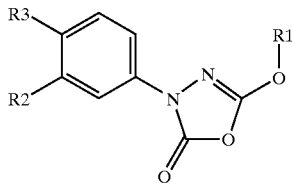

1 in which
$R^1$ is $C_1$–$C_6$-alkyl or $C_3$–$C_9$-cycloalkyl, where both groups are unsubstituted or mono- or polysubstituted by O—$C_1$–$C_4$-alkyl, S—$C_1$–$C_4$-alkyl, N($C_1$–$C_4$-alkyl)$_2$ and/or phenyl which for its part may be mono- or polysubstituted by halogen, $C_1$–$C_4$-alkyl, O—$C_1$–$C_4$-alkyl, nitro, $CF_3$, and $R^2$ and $R^3$ independently of one another are hydrogen, $C_6$–$C_{10}$-aryl, $C_3$–$C_8$-cycloalkyl, optionally $C_1$–$C_4$-alkyl-substituted $C_6$–$C_{10}$-aryloxymethyl, O—$C_3$–$C_8$-cycloalkyl, O—$C_6$–$C_{10}$-aryl or O-benzyl, unsubstituted or mono- or polysubstituted by halogen, $CF_3$ or $C_1$–$C_4$-alkyl, O—$C_1$–$C_6$-alkyl which is mono- or polysubstituted by fluorine, $C_6$–$C_{10}$-aryl or amino, where amino for its part may be mono- or polysubstituted by $C_1$–$C_4$-alkyl, are $SO_2$—NH—$C_1$–$C_6$-alkyl, unsubstituted or substituted by N($C_1$–$C_6$-alkyl)$_2$, are $SO_2$—NH-(2,2,6,6-tetramethylpiperidin4-yl), $SO_2$—NH—$C_3$–$C_8$-cycloalkyl, unsubstituted or mono- or polysubstituted by $C_1$–$C_4$-alkyl, are $SO_2$—N($C_1$–$C_6$-alkyl)$_2$ or COX, where X is O—$C_1$–$C_6$-alkyl, NH—$C_1$–$C_6$-alkyl, NH—$C_3$–$C_8$-cycloalkyl or N($C_1$–$C_6$-alkyl)$_2$, and N($C_1$–$C_6$-alkyl)$_2$ may also be pyrrolidino, piperidino, morpholino, thiomorpholino or piperazino -which may be unsubstituted or substituted by $C_1$–$C_4$-alkyl, benzyl, $C_6$–$C_{10}$-aryl, CO—$C_1$–$C_4$-alkyl, CO—$C_6$–$C_{10}$-aryl, CO—O—$C_1$–$C_4$-alkyl, $SO_2$—$C_1$–$C_4$-alkyl or $SO_2$—$C_6$–$C_{10}$-aryl, with the proviso that $R^2$ and $R^3$ are not simultaneously hydrogen, and their physiologically acceptable salts and optical isomers.

The aryl radicals mentioned can be unsubstituted or mono- or polysubstituted by $C_1$–$C_4$-alkyl, $C_1$–$C_4$-alkoxy, halogen, trifluoromethyl. The cycloalkyl radicals mentioned can be unsubstituted or mono- or polysubstituted by $C_1$–$C_4$-alkyl, and the alkyl radicals mentioned can be substituted by hydroxyl, di-$C_1$–$C_4$-alkylamino and fluorine. Halogen denotes fluorine, chlorine, bromine, preferably fluorine and chlorine.

Preference is given to substituted 3-phenyl-5-alkoxy-1,3,4-oxadiazol-2-ones of the formula 1, in which one of the radicals $R^2$ or $R^3$ is hydrogen.

Particular preference is given to substituted 3-phenyl-5-alkoxy-1,3,4-oxadiazol-2-ones of the formula 1, in which $R^1$ is $C_1$–$C_6$-alkyl which may be unsubstituted or substituted by phenyl.

Particular preference is furthermore given to substituted 3-phenyl-5-alkoxy-1,3,4-oxadiazol-2-ones of the formula 1, in which $R^2$ and $R^3$ independently of one another are hydrogen, $C_6$–$C_{10}$-aryl, $C_3$–$C_8$-cycloalkyl, unsubstituted or $C_1$–$C_4$-alkyl-substituted $C_6$–$C_{10}$-aryloxymethyl, O—$C_3$–$C_8$-cycloalkyl, O—$C_6$–$C_{10}$-aryl or O-benzyl, unsubstituted or mono- or polysubstituted by $C_1$–$C_4$-alkyl or halogen, O—$C_1$–$C_6$-alkyl which is mono- or polysubstituted by fluorine, $C_6$–$C_{10}$-aryl or amino, where amino for its part may be mono- or polysubstituted by $C_1$–$C_4$-alkyl, are $SO_2$—NH—$C_1$–$C_6$-alkyl, optionally substituted by N($C_1$–$C_6$-alkyl)$_2$, are $SO_2$—NH—(2,2,6,6-tetramethylpiperidin4-yl), $SO_2$—NH—$C_3$–$C_8$-cycloalkyl, substituted by $C_1$–$C_4$-alkyl, are $SO_2$—N($C_1$–$C_6$-alkyl)$_2$ or CO—N($C_1$–$C_6$-alkyl)$_2$, and N($C_1$–$C_6$-alkyl)$_2$ may also be piperidino, morpholino or piperazino which can be unsubstituted or substituted by $C_1$–$C_4$-alkyl.

Very particular preference is also given to substituted 3-phenyl-5-alkoxy-1,3,4-oxadiazol-2-ones of the formula 1, in which $R^2$ is hydrogen, $C_6$–$C_{10}$-aryl, O—$C_6$–$C_{10}$-aryl, unsubstituted or $C_1$–$C_4$-alkyl-substituted $C_6$–$C_{10}$-aryloxymethyl, O-benzyl, is O—$C_1$–$C_6$-alkyl which is mono- or polysubstituted by fluorine or amino, where amino for its part may be mono- or polysubstituted by $C_1$–$C_4$-alkyl, is O—$C_3$–$C_8$-cycloalkyl which is unsubstituted or mono- or polysubstituted by $C_1$–$C_4$-alkyl, and $R^3$ is hydrogen, $C_6$–$C_{10}$-aryl, $C_3$–$C_8$-cycloalkyl, O—$C_3$–$C_8$-cycloalkyl or O—$C_6$–$C_{10}$-aryl which is unsubstituted or mono- or polysubstituted by $C_1$–$C_4$-alkyl or halogen, is O—$C_1$–$C_6$-alkyl which is mono- or polysubstituted by fluorine, is $SO_2$—NH—$C_1$–$C_6$-alkyl, unsubstituted or substituted by N($C_1$–$C_6$-alkyl)$_2$, is $SO_2$—NH-(2,2,6,6-tetramethylpiperidin-4-yl), $SO_2$—NH—$C_3$–$C_8$-cycloalkyl, mono- or polysubstituted by $C_1$–$C_4$-alkyl, is $SO_2$—N($C_1$–$C_6$-alkyl)$_2$ or CO—N($C_1$–$C_6$-alkyl)$_2$, and N($C_1$–$C_6$-alkyl)$_2$ is also piperidino, morpholino or piperazino, which may be unsubstituted or substituted by $C_1$–$C_4$-alkyl.

Very particular preference is given to substituted 3-phenyl-5-alkoxy-1,3,4-oxadiazol-2-ones of the formula 1, in which $R^1$ is methyl, ethyl, butyl, isopropyl or benzyl and $R^2$ is hydrogen, trifluoromethoxy, trifluorobutoxy, 3,3,5,5-tetramethylcyclohexyloxy, benzyloxy, phenoxy, phenyl, 2-diethylaminoethyloxy or 3-methylphenoxymethyl, and $R^3$ is hydrogen, trifluoromethoxy, 3,3,5,5-tetramethylcyclohexyloxy, phenoxy, 4-chlorophenoxy, cyclohexyl, phenyl, morpholinosulfonyl, 3,3,5-trimethylcyclohexylaminosulfonyl, 2,2,6,6-tetramethylpiperidin-4-yl-aminosulfonyl, 2-(diisopropylaminoethyl)aminosulfonyl, 4-methylpiperazin-1-yl-sulfonyl, 3,3-dimethylpiperidinocarbonyl or 3,5-dichlorophenoxy.

Very particular preference is furthermore given to substituted 3-phenyl-5-alkoxy-1,3,4-oxadiazol-2-ones of the formula 1, in which $R^1$ is methyl, ethyl, butyl, isopropyl or benzyl and $R^2$ is hydrogen, trifluoromethoxy, 3,3,5,5-tetramethylcyclohexyloxy, 3 benzyloxy or phenoxy and $R^3$ is hydrogen, trifluoromethoxy, 3,3,5,5-tetramethylcyclohexyloxy, phenoxy, cyclohexyl, phenyl, morpholinosulfonyl or 3,3,5-trimethylcyclohexylaminosulfonyl.

The compounds of the formula 1 according to the invention have an unexpected inhibitory effect on the hormone-sensitive lipase HSL, an allosteric enzyme in adipocytes which is inhibited by insulin and responsible for the degradation of fats in fat cells and thus for the transfer of fat components into the bloodstream. Thus, an inhibition of this enzyme corresponds to an insulin-like effect of the compounds according to the invention which in the end results in a reduction of free fatty acids in the blood and of blood sugar. Accordingly, they can be used for metabolic disorders such as, for example, for non-insulin-dependent diabetes mellitus, for diabetic syndrome and in cases where the pancreas is damaged directly.

The compounds of the formula 1 according to the invention can be prepared by different routes using methods known per se.

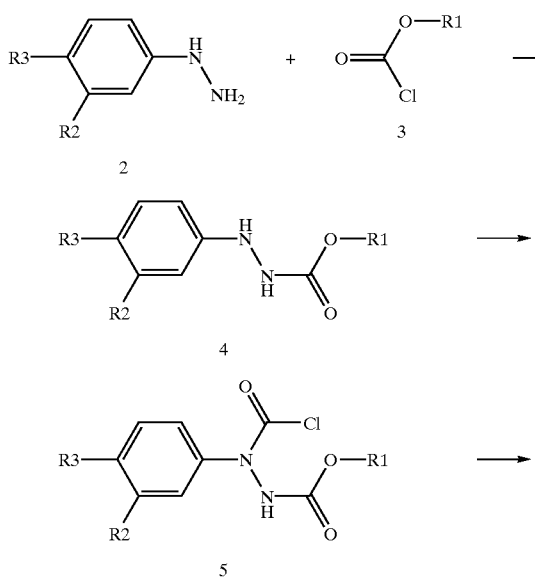

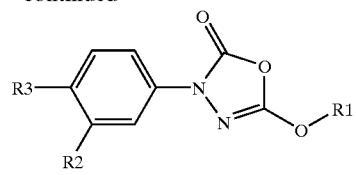

For example, the substituted 3-phenyl-5-alkoxy-1,3,4-oxadiazol-2-ones of the formula 1 can be prepared by reacting hydrazines of the formula 2 with chloroformic esters of the formula 3 or other reactive carbonic acid ester derivatives, in which $R^1$, $R^2$ and $R^3$ are as defined above, to give compounds of the formula 4 which are acylated with phosgene, carbonyldiimidazole or diphosgene and cyclized to give the compounds of the formula 1. Since in general acids are liberated in these reactions, it is recommended to add bases such as pyridine, triethylamine, aqueous sodium hydroxide solution or alkali metal carbonates to accelerate the reaction. The reactions can be carried out in wide temperature ranges. In general, it has been found to be advantageous to carry out the reactions at from 0° C. to the boiling point of the solvent used. Suitable solvents are, for example, methylene chloride, THF, DMF, toluene, ethyl acetate, n-heptane, dioxane, diethylether.

The hydrazines of the formula 2 are commercially available or can be prepared by known methods, for example by diazotization of the corresponding anilines

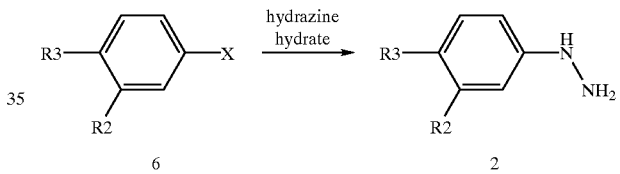

with subsequent reduction or by nucleophilic substitution of appropriately substituted phenyl derivatives 6(X=F, Cl, Br, I, $OSO_2CF_3$) with hydrazine hydrate. Such suitable phenyl derivatives can be nitro-substituted halogenated benzenes, preferably fluoro- and chloronitrobenzenes, from which, at a suitable point in the synthesis path, the compounds according to the invention can be prepared by reduction and reaction with acylating or alkylating agents, such as, for example, acid chlorides, anhydrides, isocyanates, chloroformic esters, sulfonyl chlorides or alkyl halides and arylalkyl halides.

The invention also relates to the use of compounds of the formula I in the form of their racemates, racemic mixtures and pure enantiomers, and to their diastereomers and mixtures thereof.

Pharmaceutically acceptable salts are particularly suitable for medical applications because of their greater solubility in water compared with the initial compounds on which they are based. These salts must have a pharmaceutically acceptable anion or cation. Suitable pharmaceutically acceptable acid addition salts of the compounds of the formula I are salts of inorganic acids such as hydrochloric acid, hydrobromic acid, phosphoric, metaphosphoric, nitric and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic, tartaric and trifluoroacetic acids. It is particularly preferred to use the chloride for medical purposes. Suitable pharmaceutically acceptable basic salts are ammonium salts, alkali metal salts (such as sodium and potassium salts) and alkaline earth metal salts (such as magnesium and calcium salts).

Salts with a pharmaceutically unacceptable anion likewise fall within the scope of the invention as useful intermediates for preparing or purifying pharmaceutically acceptable salts and/or for use in non-therapeutic, for example in vitro, applications.

The term "physiologically functional derivative" used herein refers to any physiologically tolerated derivative of a compound according to the invention, for example an ester, which is able on administration to a mammal, such as, for example, to humans, to form (directly or indirectly) such a compound or an active metabolite thereof.

A further aspect of this invention is the use of prodrugs of compounds of the formula I. Such prodrugs can be metabolized in vivo to a compound of the formula I. These prodrugs may themselves be active or not.

The compounds of the formula I may also exist in various polymorphous forms, for example as amorphous and crystalline polymorphous forms. All polymorphous forms of the compounds of the formula I fall within the scope of the invention and are a further aspect of the invention.

All references hereinafter to "compound(s) of the formula (I)" refer to compound(s) of the formula (I) as described above and to the salts, solvates and physiologically functional derivatives thereof as described herein.

The amount of a compound of the formula (I) necessary to achieve the desired biological effect depends on a number of factors, for example the specific compound chosen, the intended use, the mode of administration and the clinical condition of the patient. The daily dose is generally in the range from 0.3 mg to 100 mg (typically from 3 mg to 50 mg) per day and per kilogram body weight, for example 3–10 mg/kg/day. An intravenous dose may be, for example, in the range from 0.3 mg to 1.0 mg/kg, which can suitably be administered as infusion of 10 ng to 100 ng per kilogram and per minute. Infusion solutions suitable for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single dose formulations which can be administered orally, such as, for example, tablets or capsules, may contain, for example, from 1.0 to 1000 mg, typically from 10 to 600 mg. In the case of pharmaceutically acceptable salts, the above weight data are based on the weight of the free compound derived from the salt. The compounds of the formula (I) can be used for prophylaxis or therapy of the abovementioned states themselves as compound, but they are preferably in the form of a pharmaceutical composition with a compatible carrier. The carrier must, of course, be compatible in the sense of compatibility with other ingredients of the composition and not be harmful to the patient's health. The carrier may be a solid or a liquid or both and is preferably formulated with the compound as single dose, for example as tablet, which may contain from 0.05% to 95% by weight of the active ingredient. Further pharmaceutically active substances may likewise be present, including further compounds of the formula (I). The pharmaceutical compositions according to the invention may be produced by one of the known pharmaceutical methods which essentially consists of mixing the ingredients with pharmacologically acceptable carriers and/or excipients.

Pharmaceutical compositions according to the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of the formula (I) used in each case. Coated formulations and coated slow-release formulations also fall within the scope of the invention. Acid- and gastric fluid-resistant formulations are preferred. Suitable gastric fluid-resistant coatings comprise cellulose acetate phthalate, polyvinyl acetate phthalate, hydroxypropylmethylcellulose phthalate and anionic polymers of methacrylic acid and methyl methacrylate.

Suitable pharmaceutical compounds for oral administration may be in the form of separate units such as, for example, capsules, cachets, pastilles or tablets, each of which contains a defined amount of the compound of the formula (I); as powder or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. In general, the compositions are produced by uniform and homogeneous mixing of the active ingredient with a liquid and/or finely dispersed solid carrier, after which the product is shaped if necessary. Thus, for example, a tablet can be produced by compressing or shaping the powder or granules of the compound, where appropriate with one or more additional ingredients. Compressed tablets may be produced by tabletting the compound in free-flowing form, such as, for example, a powder or granules, where appropriate mixed with a binder, lubricant, inert diluent and/or one (or more) surface-active/dispersing agents in a suitable machine. Shaped tablets can be produced by shaping, in a suitable machine, the compound which is in powder form and has been moistened with an inert liquid diluent.

Pharmaceutical compositions suitable for peroral (sublingual) administration comprise suckable tablets which contain a compound of the formula (I) with a flavoring, normally sucrose, and gum arabic or tragacanth, and pastilles which contain the compound in an inert base such as gelatin and glycerol or sucrose and gum arabic.

Suitable pharmaceutical compositions for parenteral administration comprise preferably sterile aqueous preparations of a compound of the formula (I), which are preferably isotonic with the blood of the intended recipient. These preparations are preferably administered intravenously, although administration can also take place by subcutaneous, intramuscular or intradermal injection. These preparations can preferably be produced by mixing the compound with water and making the resulting solution sterile and isotonic. Injectable compositions according to the invention generally contain from 0.1 to 5% by weight of the active compound.

Suitable pharmaceutical compositions for rectal administration are preferably in the form of single-dose suppositories. These can be produced by mixing a compound of the formula (I) with one or more conventional solid carriers, for example cocoa butter, and shaping the resulting mixture.

Suitable pharmaceutical compositions for topical use on the skin are preferably in the form of an ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Suitable pharmaceutical compositions for transdermal applications may be in the form of single plasters which are suitable for long-term close contact with the patient's epidermis. Plasters of this type suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. As a particular option, the active ingredient can be released by electrotransport or iontophoresis as described, for example, in Pharmaceutical Research, 2 (6): 318 (1986).

The activity of the compounds of the formula 1 according to the invention was examined using the following enzyme test system:

Enzyme Preparation

Preparation of the Partially Purified HSL:

Isolated rat fat cells are obtained from epididymal fatty tissue from untreated male rats (Wistar, 220–250 g) by collagenase treatment according to published processes (e.g. S. Nilsson et al., Anal. Biochem. 158, 1986, 399–407; G. Fredrikson et al., J. Biol. Chem. 256, 1981, 6311–6320; H. Tornquist et al., J. Biol. Chem. 251, 1976, 813–819). The fat cells from 10 rats are washed three times by flotation with 50 ml each of homogenization buffer (25 ml tris/HCl, pH 7.4, 0.25 M sucrose, 1 mM EDTA, 1 mM DTT, 10 $\mu$g/ml of leupeptin, 10 $\mu$g/ml of antipain, 20 $\mu$g/ml of pepstatin) and finally taken up in 10 ml of homogenization buffer. The fat cells are homogenized in a Teflon-in-glass homogenizer (Braun-Melsungen) by 10 strokes at 1500 rpm and 15° C. The homogenizate is centrifuged (Sorvall SM24 tubes, 5000 rpm, 10 min, 4° C). The bottom layer between the overlying fatty layer and the pellet is removed and the centrifugation is repeated. The bottom layer resulting from this is centrifuged again (Sorvall SM24 tubes, 20,000 rpm, 45 min, 4° C). The bottom layer is removed and treated with 1 g of heparin-Sepharose (Pharmacia Biotech, CL-6B, washed 5× with 25 mM tris/HCl, pH 7.4, 150 mM NaCl). After incubation for 60 min at 4° C. (shake at intervals of 15 min), the batch is centrifuged (Sorvall SM24 tubes, 3000 rpm, 10 min, 4° C.). The supernatant is brought to pH 5.2 by addition of glacial acetic acid and incubated at 4° C. for 30 min. The precipitates are collected by centrifugation (Sorvall SS34, 12,000 rpm, 10 min, 4° C.) and suspended in 2.5 ml of 20 mM tris/HCl, pH 7.0, 1 mM EDTA, 65 mM NaCl, 13% sucrose, 1 mM DTT, 10 $\mu$g/ml of leupeptin/pepstatin/antipain. The suspension is dialyzed overnight at 4° C. against 25 mM tris/HCl, pH 7.4, 50% glycerol, 1 mM DTT, 10 $\mu$g/ml of leupeptin, pepstatin, antipain and then applied to a hydroxylapatite column (0.1 g per 1 ml of suspension, equilibrated with 10 mM potassium phosphate, pH 7.0, 30% glycerol, 1 mM DTT). The column is washed with four volumes of equilibration buffer at a flow rate of 20 to 30 ml/h. The HSL is eluted with a volume of equilibration buffer which contains 0.5 M potassium phosphate, then dialyzed (see above) and concentrated 5 to 10 times by ultrafiltration (Amicon Diaflo PM 10 filter) at 4° C. The partially purified HSL can be stored at −70° C. for 4 to 6 weeks.

Assay:

For the preparation of the substrate, 25–50 $\mu$Ci of [$^3$H] trioleoylglycerol (in toluene), 6.8 $\mu$Mol of unlabeled trioleoylglycerol and 0.6 mg of phospholipids (phosphatidylcholine/phosphatidylinositol 3:1 w/v) are mixed, dried over $N_2$ and then taken up in 2 ml of 0.1 M $KP_i$ (pH 7.0) by ultrasonic treatment (Branson 250, microtip, setting 1–2, 2×1 min at a 1 min interval). After addition of 1 ml $KP_i$ and fresh ultrasonic treatment (4×30 sec on ice at 30 sec intervals), 1 ml of 20% BSA (in $KP_i$) is added (final concentration of trioleoylglycerol 1.7 mM). For the reaction, 100 $\mu$l of substrate solution are pipetted into 100 $\mu$l of HSL solution (HSL prepared as above, diluted in 20 mM $KP_i$, pH 7.0, 1 mM EDTA, 1 mM DTT, 0.02% BSA, 20 $\mu$g/ml of pepstatin, 10 $\mu$g/ml of leupeptin) and incubated at 37° C. for 30 min. After addition of 3.25 ml of methanol/chloroform/heptane (10:9:7) and of 1.05 ml of 0.1 M $K_2CO_3$, 0.1 M boric acid (pH 10.5), the batch is well mixed and finally centrifuged (800×g, 20 min). After phase separation, one equivalent of the upper phase (1 ml) is taken and the radioactivity is determined by liquid scintillation measurement.

Analysis:

Substances are customarily tested in four independent batches. The inhibition of the enzymatic activity of the HSL by a test substance is determined by comparison with an uninhibited control reaction. The $IC_{50}$ value is calculated by means of an inhibition curve using at least 10 concentrations of the test substance. For the analysis of the data, the software package GRAPHIT, Elsevier-BIOSOFT is used.

In this test, the compounds had the following activity:

| Compound Example No. | $IC_{50}$ ($\mu$M) |
| --- | --- |
| 8 | 15 |
| 10 | 6 |
| 11 | 10 |
| 12 | 10 |
| 13 | 10 |
| 14 | 50 |
| 15 | 2 |
| 16 | 2 |
| 17 | 2 |
| 18 | <1 |
| 19 | 5 |
| 33 | 4 |
| 34 | 3 |
| 35 | 3 |
| 36 | 2 |
| 37 | 3 |
| 38 | <1 |
| 39 | 60 |

The examples below illustrate the preparation methods in more detail without limiting them.

EXAMPLES

Example 1

4-Fluorobenzenesulfonic Acid Morpholide (Intermediate)

20 g of morpholine were added dropwise to a solution, cooled with ice, of 19.5 g of 4-fluorobenzenesulfonyl chloride in 100 ml of toluene, and the mixture was heated under reflux for 1 hour. After cooling, the mixture was concentrated under reduced pressure, the residue was stirred with water and the precipitate was filtered off with suction, washed with water and recrystallized from isopropanol.

Yield:16.9 g m.p.: 140° C.

Example 2

4-Hydrazinobenzenesulfonic Acid Morpholide (Intermediate)

5 g of 4-fluorobenzenesulfonic acid morpholide were dissolved in 15 ml of N-methylpyrrolidone and mixed with 2.5 g of hydrazine hydrate, and the mixture was heated at 100° C. for 1 hour. After cooling to room temperature, 75 ml of water were added and the mixture was stirred at room temperature. After 2 hours, the solid was filtered off with suction and recrystallized from isopropanol.

Yield: 3.2 g m.p.: 164° C.

The following example was prepared in a similar manner:

Example 3
N-(3,3,5-Trimethylcyclohexyl)-4-hydrazinobenzenesulfonamide (Intermediate)

m.p.: 129° C.

Example 4
4-(3,3,5,5-Tetramethylcyclohexyloxy)nitrobenzene (Intermediate)

1.3 g of sodium hydride are added to a solution of 7.8 g of 3,3,5,5-tetramethylcyclohexanol in 50 ml of dimethylformamide, and the mixture is stirred at 40–50° C. for 30 min. A total of 7.0 g of 4-fluoronitrobenzene are then added a little at a time, and the mixture is subsequently heated at 100° C. for three hours and cooled to room temperature. 250 ml of ice-water are added, the mixture is stirred and the resulting solid is filtered off with suction and dried under reduced pressure.

Yield: 8.6 g m.p.: 70° C.

Example 5
4-(3,3,5,5-Tetramethylcyclohexyloxy)aniline (Intermediate)

Under atmospheric pressure, 8.3 g of 4-(3,3,5,5-tetramethylcyclohexyloxy) nitrobenzene in 500 ml of methanol are hydrogenated in the presence of 400 mg of platinum dioxide until the uptake of hydrogen has ended. The catalyst is filtered off, the solution is then concentrated using a rotary evaporator and the residue, a brownish oil which slowly solidifies, is used for the further reactions without any further purification.

Yield: 7.3 g

Example 6
4-(3,3,5,5-Tetramethylcyclohexyloxy)phenylhydrazine Hydrochloride (Intermediate)

A stirred mixture, cooled to −10° C., of 3.7 g of 4-(3,3,5,5-tetramethylcyclohexyloxy)aniline, 7.5 ml of water and 15.5 ml of conc. HCl is mixed dropwise with a solution of 1.13 g of sodium nitrite in 7.5 ml of water, and the mixture is stirred at −10° C. for 45 min and subsequently added dropwise to a suspension of 9.3 g of tin dichloride dihydrate in 7 ml of conc. HCl. The precipitate is filtered off with suction, washed with water, suspended under nitrogen in 200 ml of water and decomposed at 10–15° C. using 100 ml of 30% strength aqueous sodium hydroxide solution. The precipitate that is then formed is filtered off with suction, washed with water, taken up in 200 ml of ether and dried with sodium sulfate. The product is precipitated using ethereal HCl, filtered off with suction and dried under reduced pressure.

Yield: 2.1 g m.p.: 171° C.

Example 7
Ethyl N'-(4-Morpholinosulfonylphenyl)hydrazinoformate (Intermediate)

With ice-cooling, 114 mg of ethyl chloroformate were carefully added dropwise to a mixture of 0.275 g of 4-hydrazinobenzenesulfonic acid morpholide, 5 ml of methylene chloride and 1 ml of pyridine, and the mixture was then stirred and slowly warmed to RT. After dilution with 10 ml of water, the product was extracted with ethyl acetate and the ethyl acetate phase was washed repeatedly with water, dried over sodium sulfate and concentrated. The resulting oily crude product was reacted further without further purification.

Yield: 0.25 g

Example 8
3-(4-Morpholinosulfonylphenyl)-5-ethoxy-1,3,4-oxadiazol-2-one

The oil from Example 3 was taken up in 5 ml of methylene chloride and, with stirring and ice-cooling, admixed with 1 ml of a 20% strength solution of phosgene and toluene. This mixture was allowed to stand at room temperature overnight and diluted with a further 10 ml of methylene chloride and then washed 3 times with water. After drying over sodium sulfate, the mixture was concentrated under reduced pressure and the product was purified by column chromatography (silica gel, solvent: methanol: methylene chloride=2:98).

Yield:130 mg m.p.: 195° C.

The following examples were prepared similarly to Example 4:

Example 9
3-(4-Morpholinosulfonylphenyl)-5-methoxy-1,3,4-oxadiazol-2-one m.p.: 164° C.

Example 10
3-(4-Trifluoromethoxyphenyl)-5-methoxy-1,3,4-oxadiazol-2-one m.p.: 52° C.

Example 11
3-(4-Trifluoromethoxyphenyl)-5-ethoxy-1,3,4-oxadiazol-2-one m.p.: 63° C.

Example 12
3-(4-Trifluoromethoxyphenyl)-5-isopropoxy-1,3,4-oxadiazol-2-one m.p.: Oil

Example 13
3-(4-Trifluoromethoxyphenyl)-5-butoxy-1,3,4-oxadiazol-2-one m.p.: Oil

Example 14
3-(4-Trifluoromethoxyphenyl)-5-benzyloxy-1,3,4-oxadiazol-2-one m.p.: Oil

Example 15
3-(4-(3,3,5-Trimethylcyclohexylaminosulfonyl)phenyl)-5-methoxy-1,3,4-oxadiazol-2-one m.p.: 164° C.

Example 16
3-(4-(3,3,5,5-Tetramethylcyclohexyloxy)phenyl)-5-ethoxy-1, 3,4-oxadiazol-2-one m.p.: 111° C.

Example 17
3-(3-Benzyloxyphenyl)-5-methoxy-1,3,4-oxadiazol-2-one m.p.: Oil

Example 18
3-(3-Benzyloxyphenyl)-5-ethoxy-1,3,4-oxadiazol-2-one m.p.: 85° C.

Example 19
3-(3-Trifluoromethoxyphenyl)-5-ethoxy-1,3,4-oxadiazol-2-one m.p.: Oil

Example 20
3-(3-Trifluoromethoxyphenyl)-5-methoxy-1,3,4-oxadiazol-2-one
 m.p.: Oil

Example 21
3-(3-Trifluoromethoxyphenyl)-5-isopropoxy-1,3,4-oxadiazol-2-one
 m.p.: Oil

Example 22
3-(4-(2,2,6,6-Tetramethylpiperidin-4-yl-aminosulfonyl)phenyl)-5-methoxy-1,3,4-oxadiazol-2-one
 m.p.: Resin

Example 23
3-(4-(2,2,6,6-Tetramethylpiperidin-4-yl-aminosulfonyl)phenyl)-5-isopropoxy-1,3,4-oxadiazol-2-one
 m.p.: Resin

Example 24
3-(4-(2-(Diisopropylaminoethyl)aminosulfonyl)phenyl)-5-methoxy-1,3,4-oxadiazol-2-one
 m.p.: Oil

Example 25
3-(4-(2-(Diisopropylaminoethyl)aminosulfonyl)phenyl)-5-isopropoxy-1,3,4-oxadiazol-2-one
 m.p.: Oil

Example 26
3-(4-(4-Methylpiperazin-1-yl-sulfonyl)phenyl)-5-isopropoxy-1,3,4-oxadiazol-2-one
 m.p.: Resin

Example 27
3-(4-(4-Methylpiperazin-1-yl-sulfonyl)phenyl)-5-methoxy-1,3,4-oxadiazol-2-one
 m.p.: Resin

Example 28
3-(3-(4,4,4-Trifluorobutyloxy)phenyl)-5-ethoxy-1,3,4-oxadiazol-2-one
 m.p.: Oil

Example 29
3-(3-(2-Diethylaminoethyloxy)phenyl)-5-ethoxy-1,3,4-oxadiazol-2-one
 m.p.: Resin

Example 30
3-(4-(4-Chlorophenoxy)phenyl)-5-methoxy-1,3,4-oxadiazol-2-one
 m.p.: 68° C.

Example 31
3-(4-(4-Chlorophenoxy)phenyl)-5-isopropoxy-1,3,4-oxadiazol-2-one
 m.p.: Oil

Example 32
3-(4-(3,3,5-Trimethylcyclohexylaminosulfonyl)phenyl)-5-isopropoxy-1,3,4-oxadiazol-2-one
 m.p.: Oil

Example 33
3-(3-Phenoxyphenyl)-5-methoxy-1,3,4-oxadiazol-2-one
 m.p.: 89° C.

Example 34
3-(3-Phenoxyphenyl)-5-ethoxy-1,3,4-oxadiazol-2-one
 m.p.: 50° C.

Example 35
3-(3-Phenoxyphenyl)-5-isopropoxy-1,3,4-oxadiazol-2-one
 m.p.: 58° C.

Example 36
3-(4-Phenoxyphenyl)-5-methoxy-1,3,4-oxadiazol-2-one
 m.p.: 83° C.

Example 37
3-(4–Cyclohexylphenyl)-5-methoxy-1,3,4-oxadiazol-2-one
 m.p.: Resin

Example 38
3-(3-(3,3,5,5-Tetramethylcyclohexyloxy)phenyl)-5-methoxy-1,3,4-oxadiazol-2-one
 m.p.: 68° C.

Example 39
3-(4-Phenylphenyl)-5-methoxy-1,3,4-oxadiazol-2-one
 m.p.:>260° C. (decomp.)

Example 40
3-(3-(3-Methylphenoxymethyl)phenyl)-5-methoxy-1,3,4-oxadiazol-2-one
 m.p.: 47° C.

Example 41
3-(3-Phenylphenyl)-5-methoxy-1,3,4-oxadiazol-2-one
 m.p.: 80° C.

Example 42
3-(4-(3,3-Dimethylpiperidinocarbonyl)phenyl)-5-methoxy-1,3,4-oxadiazol-2-one
 m.p.: Resin

Example 43
3-(4-(3,3,5,5-Tetramethylcyclohexyloxy)phenyl)-5-isopropoxy-1,3,4-oxadiazol-2-one
 m.p.: Resin

We claim:
1. A substituted 3-phenyl-5-alkoxy-1,3,4-oxadiazol-2-one of the formula 1,

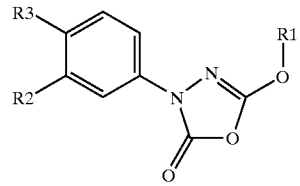

in any optically isomeric form, or a physiologically acceptable salt thereof, in which
  $R^1$ is $C_1$–$C_6$-alkyl or $C_3$–$C_9$-cycloakyl, where both groups are unsubstituted or mono- or polysubstituted by O—$C_1$–$C_4$-alkyl, S—$C_1$–$C_4$-alkyl, N($C_1$–$C_4$-alkyl)$_2$ and/or phenyl which for its part is unsubstituted or mono- or polysubstituted by halogen, $C_1$–$C_4$-alkyl, O—$C_1$–$C_4$-alkyl, nitro, or $CF_3$, and
  $R^2$ and $R^3$ independently of one another are hydrogen; $C_6$–$C_{10}$-aryl; $C_3$–$C_8$-cycloalkyl; unsubstituted or $C_1$–$C_4$-alkyl-substituted $C_6$–$C_{10}$-aryloxymethyl; O—$C_3$–$C_8$-cycloalkyl, O—$C_6$–$C_{10}$-aryl or O-benzyl, unsubstituted or mono- or polysubstituted by halogen, $CF_3$ or $C_1$–$C_4$-alkyl;

O—$C_1$–$C_6$-alkyl which is mono- or polysubstituted by fluorine, $C_6$–$C_{10}$-aryl or amino, where amino for its part is unsubstituted or mono- or polysubstituted by $C_1$–$C_4$-alkyl;

$SO_2$—NH—$C_1$–$C_6$-alkyl, unsubstituted or substituted by N($C_1$–$C_6$-alkyl)$_2$;

$SO_2$—NH—$C_3$–$C_8$-cycloalkyl, unsubstituted or mono- or polysubstituted by $C_1$–$C_4$-alkyl;

$SO_2$—N($C_1$–$C_6$-alkyl)$_2$ or COX, where X is O—$C_1$–$C_6$-alkyl, NH—$C_1$–$C_6$-alkyl, NH—$C_3$–$C_8$-cycloalkyl or N($C_1$–$C_6$-alkyl)$_2$, with the proviso that $R^2$ and $R^3$ are not simultaneously hydrogen.

2. The substituted 3-phenyl-5-alkoxy-1,3,4-oxadiazol-2-one as claimed in claim 1, in which one of the radicals $R^2$ or $R^3$ is hydrogen.

3. The substituted 3-phenyl-5-alkoxy-1,3,4-oxadiazol-2-one as claimed in claim 1, in which $R^1$ is $C_1$–$C_6$-alkyl which is unsubstituted or substituted by phenyl.

4. The substituted 3-phenyl-5-alkoxy-1,3,4-oxadiazol-2-one as claimed in claim 1, in which $R^2$ and $R^3$ independently of one another are hydrogen, $C_6$–$C_{10}$-aryl, $C_3$–$C_8$-cycloalkyl, unsubstituted or $C_1$–$C_4$-alkyl-substituted $C_6$–$C_{10}$-aryloxymethyl, O—$C_3$–$C_8$-cycloalkyl, O—$C_6$–$C_{10}$-aryl or O-benzyl, unsubstituted or mono- or polysubstituted by $C_1$–$C_4$-alkyl or halogen, O—$C_1$–$C_6$-alkyl which is mono- or polysubstituted by fluorine, $C_6$–$C_{10}$-aryl or amino, where amino for its part is unsubstituted or mono- or polysubstituted by $C_1$–$C_4$-alkyl, are $SO_2$—NH—$C_1$–$C_6$-alkyl, unsubstituted or substituted by N($C_1$–$C_6$-alkyl)$_2$, are $SO_2$—NH—$C_3$–$C_8$-cycloalkyl, substituted by $C_1$–$C_4$-alkyl, are $SO_2$—N($C_1$–$C_6$-alkyl)$_2$ or CO—N($C_1$–$C_6$-alkyl)$_2$.

5. The substituted 3-phenyl-5-alkoxy-1,3,4-oxadiazol-2-one as claimed in claim 1, in which $R^2$ is hydrogen, $C_6$–$C_{10}$-aryl, O—$C_6$–$C_{10}$-aryl, unsubstituted or $C_1$–$C_4$-alkyl-substituted $C_6$–$C_{10}$-aryloxymethyl, O-benzyl, is O—$C_1$–$C_6$-alkyl which is mono- or polysubstituted by fluorine or amino, where amino for its part is unsubstituted or mono- or polysubstituted by $C_1$–$C_4$-alkyl, is O—$C_3$–$C_8$-cycloalkyl which is unsubstituted or mono- or polysubstituted by $C_1$–$C_4$-alkyl, and $R^3$ is hydrogen, $C_6$–$C_{10}$-aryl, $C_3$–$C_8$-cycloalkyl, O—$C_3$–$C_8$-cycloalkyl or O—$C_6$–$C_{10}$-aryl which is unsubstituted or mono- or polysubstituted by $C_1$–$C_4$-alkyl or halogen, is O—$C_1$–$C_6$-alkyl which is mono- or polysubstituted by fluorine, is $SO_2$—NH—$C_1$–$C_6$-alkyl, unsubstituted or substituted by N($C_1$–$C_6$-alkyl)$_2$, is $SO_2$—NH—$C_3$–$C_8$-cycloalkyl, mono- or polysubstituted by $C_1$–$C_4$-alkyl, is $SO_2$—N($C_1$–$C_6$-alkyl)$_2$ or CO—N($C_1$–$C_6$-alkyl)$_2$.

6. The substituted 3-phenyl-5-alkoxy-1,3,4-oxadiazol-2-one as claimed in claim 1, in which $R^1$ is methyl, ethyl, butyl, isopropyl or benzyl and $R^2$ is hydrogen, trifluoromethoxy, trifluorobutoxy, 3,3,5,5-tetramethylcyclohexyloxy, benzyloxy, phenoxy, phenyl, 2-diethylaminoethyloxy or 3-methylphenoxymethyl, and $R^3$ is hydrogen, trifluoromethoxy, 3,3,5,5-tetramethylcyclohexyloxy, phenoxy, 4-chlorophenoxy, cyclohexyl, phenyl, 3,3,5-trimethylcyclohexylaminosulfonyl, 2-(diisopropylaminoethyl)aminosulfonyl or 3,5-dichlorophenoxy.

7. The substituted 3-phenyl-5-alkoxy-1,3,4-oxadiazol-2-one as claimed in claim 1, in which $R^1$ is methyl, ethyl, butyl, isopropyl or benzyl and $R^2$ is hydrogen, trifluoromethoxy, 3,3,5,5-tetramethylcyclohexyloxy, benzyloxy or phenoxy and $R^3$ is hydrogen, trifluoromethoxy, 3,3,5,5-tetramethylcyclohexyloxy, phenoxy, cyclohexyl, phenyl or 3,3,5-trimethylcyclohexylaminosulfonyl.

8. A process for preparing the substituted 3-phenyl-5-alkoxy-1,3,4-oxadiazol-2-one of the formula 1 as claimed in claim 1, which comprises reacting a hydrazine of the formula 2 below with a chloroformic ester of the formula 3 below or other reactive carbonic acid ester derivative, in which $R^1$, $R^2$ and $R^3$ are as defined in claim 1, to give a compound of the formula 4 below, acylating the compound of formula 4 with phosgene, carbonyldiimidazole or diphosgene to give a compound of the formula 5 below, and cyclizing the compound of the formula 5 to give the compound of the formula 1:

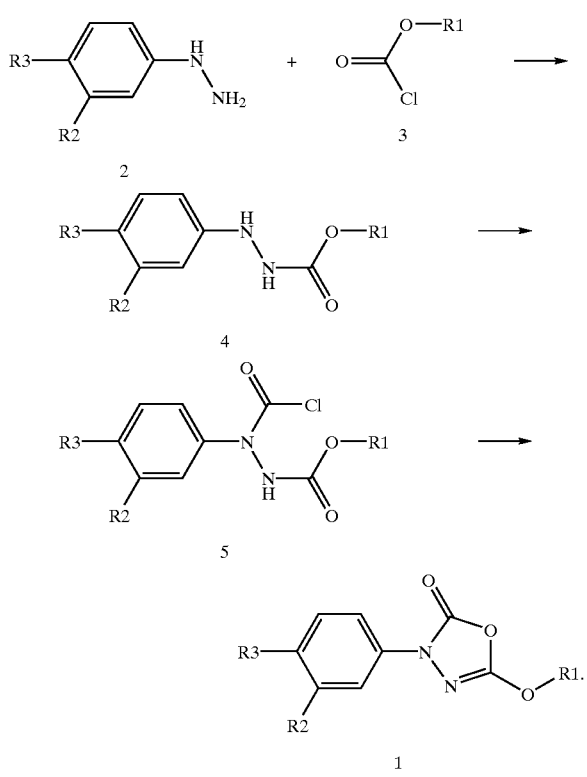

9. A method for inhibiting the hormone-sensitive lipase HSL, which comprises administering to a host in need of the inhibition an effective amount of a compound as claimed in claim 1.

10. A pharmaceutical composition, which comprises an effective amount of a compound as claimed in claim 1, together with a pharmaceutically acceptable excipient.

11. A method for treating a metabolic disorder, which comprises administering to a host in need of the treatment an effective amount of a compound as claimed in claim 1.

12. A method as claimed in claim 11, wherein the metabolic disorder is non-insulin-dependent diabetes mellitus or diabetic syndrome.

13. A method as claimed in claim 11, wherein the metabolic disorder is caused by direct damage to the pancreas.

* * * * *

UNITED STATES PATENT AND TRADEMARK OFFICE
CERTIFICATE OF CORRECTION

PATENT NO.    : 6,596,742 B1                                             Page 1 of 1
DATED         : July 22, 2003
INVENTOR(S)   : Petry et al.

It is certified that error appears in the above-identified patent and that said Letters Patent is hereby corrected as shown below:

Column 12,
Line 56, "$C_3$-$C_9$-cycloakyl" should read -- $C_3$-$C_9$-cycloalkyl --.

Signed and Sealed this

Twenty-third Day of September, 2003

JAMES E. ROGAN
*Director of the United States Patent and Trademark Office*